(12) United States Patent
Holle

(10) Patent No.: US 9,240,117 B2
(45) Date of Patent: Jan. 19, 2016

(54) MEDICAL LEAD INSERTION DETECTION BY MONITORING FOR ELECTRICAL CONTINUITY BETWEEN ADJACENT ELECTRICAL CONTACTS OF A MEDICAL DEVICE

(75) Inventor: Mark J. Holle, Shoreview, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 121 days.

(21) Appl. No.: 13/991,359

(22) PCT Filed: Nov. 18, 2011

(86) PCT No.: PCT/US2011/061426
§ 371 (c)(1),
(2), (4) Date: Jun. 3, 2013

(87) PCT Pub. No.: WO2012/082316
PCT Pub. Date: Jun. 21, 2012

(65) Prior Publication Data
US 2013/0257625 A1 Oct. 3, 2013

(51) Int. Cl.
*G08B 21/00* (2006.01)
*G08B 21/18* (2006.01)
(Continued)

(52) U.S. Cl.
CPC .............. *G08B 21/18* (2013.01); *A61N 1/3752* (2013.01); *G01R 31/026* (2013.01); *H01R 13/7031* (2013.01); *G01R 31/043* (2013.01); *H01R 13/5224* (2013.01); *H01R 24/58* (2013.01)

(58) Field of Classification Search
CPC ....... A61N 1/05; A61N 1/3752; A61N 1/055; A61N 1/37; A61N 1/37; A61N 1/058; H01R 13/5224; H01R 4/5091

USPC ................... 340/687, 650, 657, 539.1, 686.6, 340/870.01, 573.1; 607/2, 5, 126, 116, 607/36–37, 119, 115; 439/587, 372, 638, 439/620.31
See application file for complete search history.

(56) References Cited

U.S. PATENT DOCUMENTS 5,431,692 A  7/1995 Hansen et al.
5,891,179 A  4/1999 Newhall
(Continued)

FOREIGN PATENT DOCUMENTS

EP  0689854  1/1996
WO  WO00/13746  3/2000
(Continued)

OTHER PUBLICATIONS

Boston Scientific ALTRUA System Guide (2009).
(Continued)

*Primary Examiner* — Hoi Lau
(74) *Attorney, Agent, or Firm* — Withers & Keys, LLC

(57) ABSTRACT

Medical devices and systems provide for detection of proper lead insertion by monitoring for electrical continuity between adjacent electrical contacts. The electrical contacts are spaced so that an electrical connector of a medical lead being inserted will span the distance between the electrical contacts and thereby maintain a physical connection with both electrical contacts at one time. Upon the medical device detecting that continuity is achieved between the adjacent electrical contacts, the medical device may provide an indication such as a visual and/or audible cue to a clinician who is inserting the lead and/or by providing a telemetry signal to an external device such as a programmer so that the programmer may then provide a visual and/or audible cue to a technician operating the programmer.

35 Claims, 7 Drawing Sheets

(51) Int. Cl.
*A61N 1/375* (2006.01)
*G01R 31/02* (2006.01)
*H01R 13/703* (2006.01)
*G01R 31/04* (2006.01)
*H01R 13/52* (2006.01)
*H01R 24/58* (2011.01)

(56) References Cited

U.S. PATENT DOCUMENTS

| | | |
|---|---|---|
| 6,016,447 A | 1/2000 | Juran et al. |
| 6,721,600 B2 | 4/2004 | Jorgenson |
| 6,978,171 B2 | 12/2005 | Goetz et al. |
| 7,231,253 B2 | 6/2007 | Tidemand |
| 7,359,751 B1 | 4/2008 | Erickson |
| 7,493,159 B2 | 2/2009 | Hrdlicka et al. |
| 7,496,409 B2 | 2/2009 | Greenhut |
| 7,515,961 B2 | 4/2009 | Germanson |
| 7,647,110 B2 | 1/2010 | Hornfeldt |
| 2003/0073348 A1 | 4/2003 | Ries et al. |
| 2003/0174066 A1* | 9/2003 | Goetz ........... A61N 1/37211 340/870.01 |
| 2003/0174069 A1* | 9/2003 | Goetz ........... A61N 1/37252 340/870.07 |
| 2004/0064161 A1 | 4/2004 | Gunderson |
| 2004/0073266 A1 | 4/2004 | Haefner |
| 2005/0033395 A1* | 2/2005 | Seifert et al. ................ 607/126 |
| 2005/0221671 A1* | 10/2005 | Lyu et al. ..................... 439/587 |
| 2006/0089681 A1 | 4/2006 | Tumlinson |
| 2007/0018810 A1* | 1/2007 | Smythe ............. A61B 5/0031 340/539.12 |
| 2008/0183246 A1 | 7/2008 | Patel et al. |
| 2008/0262582 A1 | 10/2008 | Alexander et al. |
| 2010/0023084 A1 | 1/2010 | Gunderson |
| 2010/0106204 A1* | 4/2010 | Moffitt et al. ................... 607/2 |
| 2010/0106206 A1* | 4/2010 | Aghassian et al. ............ 607/2 |
| 2010/0137929 A1* | 6/2010 | Libbey et al. ................... 607/5 |
| 2011/0054334 A1* | 3/2011 | Fischell ........... A61B 5/0402 600/509 |
| 2012/0038477 A1 | 2/2012 | Torgerson et al. |
| 2013/0257625 A1* | 10/2013 | Holle ............................ 340/687 |
| 2014/0200642 A1* | 7/2014 | Kast et al. ..................... 607/116 |

FOREIGN PATENT DOCUMENTS

| | | |
|---|---|---|
| WO | WO02/18009 | 3/2002 |
| WO | WO2007/027568 | 3/2007 |
| WO | WO2010/127014 | 11/2010 |

OTHER PUBLICATIONS

PCT/US11/061426: search report and written opinion.
PCT/US11/032783: search report and written opinion.

* cited by examiner

MEDICAL LEAD INSERTION DETECTION BY MONITORING FOR ELECTRICAL CONTINUITY BETWEEN ADJACENT ELECTRICAL CONTACTS OF A MEDICAL DEVICE

TECHNICAL FIELD

Embodiments relate to medical devices and systems. More particularly, embodiments relate to detecting medical lead insertion within a medical device by monitoring for electrical continuity between adjacent electrical contacts of the medical device where an electrical connector of a medical lead spans the adjacent electrical contacts upon completion of medical lead insertion.

BACKGROUND

Medical systems such as those that are implantable often utilize a medical device coupled to a medical lead. The medical lead may be fully or partially implanted within the body of the patient and the medical lead extends from the internal or external site where the medical device is located to the internal site where the electrical sensing and/or stimulation will occur. A distal end of the medical lead includes electrodes that provide the sensing and/or stimulation interface to the tissue of the patient. A proximal end of the medical lead includes electrical connectors that make physical connection with electrical contacts within a header of the medical device. Electrical conductors within the medical lead carry signals between the electrical connectors and the electrodes.

Typically, the medical lead and the medical device are separate items that are coupled together once implantation of the medical lead is completed. A clinician manually inserts the proximal end of the medical lead into the header of the medical device. The proximal end of the medical lead needs to be fully inserted into the header to ensure that each electrical connector of the medical lead makes electrical connection to a corresponding electrical contact of the header. If the medical lead is not fully inserted, one or more of the electrical connectors may not make contact with a corresponding electrical contact, and as a result, a corresponding one or more electrodes of the medical lead will not be functional.

The medical lead may also be inserted too far. For the reasons stated above regarding failing to fully insert the lead, a clinician may be overly zealous when inserting the lead and may damage the lead by continuing to apply insertion force once the lead is already fully inserted. Such lead damage may also cause one or more electrodes of the medical lead to not be functional.

Various techniques have been employed to assist the clinician in determining when a lead has been fully inserted so that insertion force can be stopped. For instance, headers of the medical devices may be transparent so that the clinician may view the lead as it passes into the header. However, medical devices and medical leads continue to be miniaturized to the point that judging the location of the lead relative to the electrical contacts within the header is difficult.

Other techniques utilize impedance measurements for the electrical pathways from the electrical contacts of the header to the electrodes. These impedance measurements provide only a gross assessment in that an electrical connector may have only a slight electrical connection to an electrical contact where that slight connection may fail over time due to small movements of the medical lead within the header, yet the impedance measurement taken immediately after insertion may indicate that adequate insertion has occurred. As another drawback, these impedance measurements involve the interface of the electrodes to the tissue and this interface may provide unreliable results particularly immediately after lead implantation when lead insertion into the medical device typically occurs.

SUMMARY

Embodiments address issues such as these and others by providing a pair of electrical contacts within the medical device that are adjacent and these contacts are monitored by the medical device for the establishment of continuity between them. The electrical contacts are spaced so that an electrical connector of the medical lead may span the space so that the electrical connector may maintain contact with both electrical contacts at the same time thereby establishing electrical continuity between them. Upon continuity being detected, a notification may be generated to indicate that the lead is fully inserted.

Embodiments provide a method of detecting that a medical lead has been fully inserted into a medical device. The method involves providing a first and a second electrical contact within the medical device, the first and the second electrical contacts being adjacent and electrically isolated from each other where a spacing between the first and second electrical contacts allows for an electrical connector of the medical lead to maintain physical contact with both the first and second electrical contacts at one time. During lead insertion, the method involves monitoring for electrical continuity between the first and second electrical contacts. The method further involves providing a notification upon detecting electrical continuity between the first and second electrical contacts.

Embodiments provide an implantable medical device that includes a header and a plurality of electrical contacts within the header. The plurality of electrical contacts comprises a first electrical contact and a second electrical contact being adjacent and electrically isolated from each other where a spacing between the first and second electrical contacts allows for an electrical connector of a medical lead to maintain physical contact with both the first and the second electrical contacts at one time. The implantable medical device further includes medical circuitry electrically connected to at least one of the electrical contacts of the plurality. The implantable medical device also includes lead insertion monitoring circuitry electrically connected to the first and second electrical contacts, wherein during lead insertion, the lead insertion monitoring circuitry monitors for electrical continuity between the first and second electrical contacts and provides a notification upon detecting electrical continuity between the first and second electrical contacts.

Embodiments provide a medical system that includes an implantable medical device that comprises a header and a plurality of electrical contacts within the header, wherein the plurality of electrical contacts comprises a first electrical contact and a second electrical contact being adjacent and electrically isolated from each other. The implantable medical device, during lead insertion, monitors for electrical continuity between the first and second electrical contacts and provides a notification upon detecting electrical continuity between the first and second electrical contacts. The medical system further includes an implantable medical lead that has a proximal end positioned within the header and comprises a lead body and a plurality of connectors on the proximal end. One connector of the plurality maintains physical contact with both the first and the second electrical contacts at one time. The implantable medical lead further comprises a plurality of electrodes on a distal end and electrical conductors within the lead body providing an electrical pathway between the connectors and the electrodes.

DETAILED DESCRIPTION

Embodiments provide for detection of whether an implantable medical lead has been properly inserted into a medical device. The medical device includes adjacent electrical contacts that are spaced to allow a connector of the medical lead to maintain contact with both electrical contacts at one time to thereby provide electrical continuity between them. The medical device monitors for electrical continuity between the adjacent electrodes and then provides a notification when electrical continuity is established to thereby signal that the medical lead is properly inserted.

Figure 1:
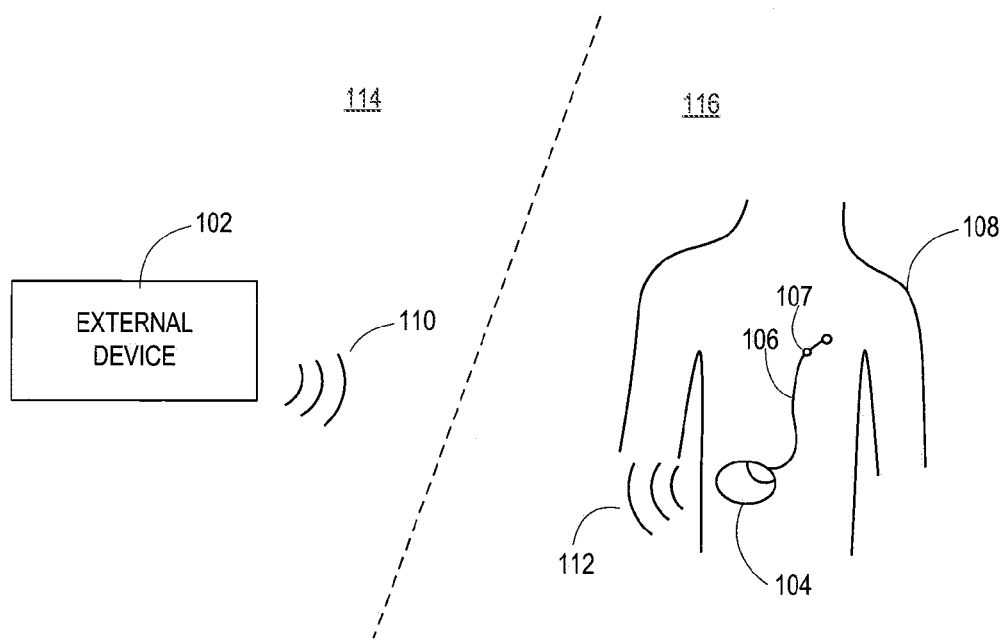
FIG. 1 shows an operating environment for illustrative embodiments that detect whether an implantable medical lead is fully inserted into a medical device.

FIG. 1 shows an external device 102 in communication with a medical device 104 that is affixed to a patient 108 either by being implanted or by an external mounting. The external device 102 may be one of various device types of a device programmer or a dedicated lead insertion detection device. Likewise, the medical device 104 may be of various device types as well such as a stimulator or a monitoring device. The medical device 104 has medical components including implantable medical leads 106 with electrodes 107 that may be used for stimulation and/or sensing that are being installed in the patient 108 and ultimately connected to the medical device 104. The medical device 104 together with the leads 106 forms a medical system.

The external device 102 and the medical device 104 typically communicate through a form of telemetry. In the case of a wireless communication link, wireless signals 110 are sent by the external device 102 and are received by the medical device 104. Likewise, wireless signals 112 are sent by the medical device 104 and are received by the external device 102. According to some embodiments, the lead insertion detection procedure may utilize the wireless communication link in one or more ways. For instance, before or during the insertion procedure, the external device 102 may instruct the medical device 104 to begin monitoring for continuity between the adjacent electrical contacts. As another example, the medical device 104 may send telemetry signals to provide a notification to the external device 102 that the lead is fully inserted so that the external device 102 may generate a notification to the operator of the external device 102. As another example, the wireless communication link may be used for both purposes.

Where the lead insertion detection procedure utilizes communication between the external device 102 and the medical device 104 during the lead insertion procedure, a form of telemetry may be used that allows separation between the wireless antenna or telemetry head of the external device 102 in an area 114 and the medical device 104 which is in an area 116 where the clinician is working. This allows the clinician to perform the lead insertion in the area 116 with no telemetry head being an obstruction to the procedure while a communication session between the external device 102 and the medical device 104 is conducted.

As an example, the telemetry may use radio frequency (RF) signaling where an antenna of the external device 102 and the medical device 104 are separated by a larger distance than occurs with near field telemetry to provide added convenience. Another example that may be used is arm's length inductive coupling telemetry where the telemetry head may be separated from the medical device 104 by a distance that prevents the telemetry head from being an obstruction to the lead insertion procedure.

Other embodiments of the lead insertion detection procedure may not utilize telemetry. For instance, the medical device 104 may be pre-configured to monitor for continuity between the adjacent electrical contacts rather than relying on an instruction from the external device 102 to activate the monitoring for continuity. Furthermore, the medical device 104 may provide the notification that continuity is detected by utilizing an on-board resource such as a speaker that provides an audible notification or a light that provides a visual notification.

Figure 2A:
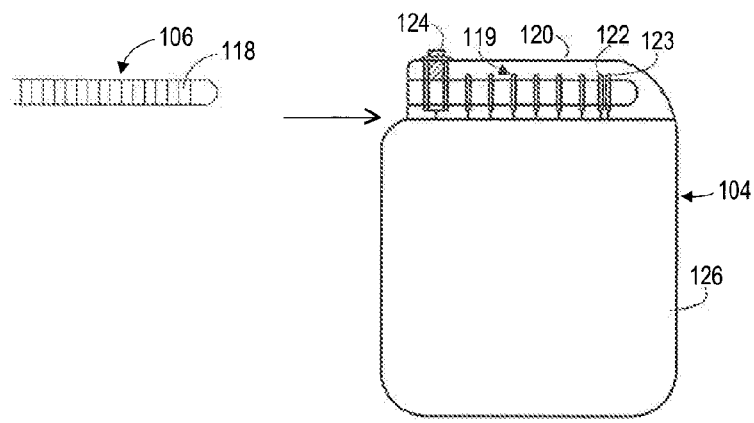
FIG. 2A shows a proximal end of an implantable lead and one example of a header of a medical device that receives the proximal end to complete electrical connections to pressure contacts.
Figure 2B:
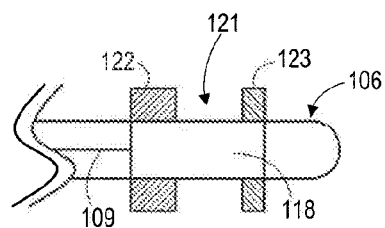
FIG. 2B shows an enlarged view of the proximal end contacts and an electrical connector from the example of FIG. 2A.

FIGS. 2A and 2B show a proximal end of the lead 106 as the lead 106 is being inserted into a header 120 of the medical device 104 that utilizes pressure contacts for detecting proper lead insertion. The header 120 is mounted to a can 126 which encloses the electrical circuitry of the medical device 104. The header 120 includes a passageway that the lead 106 enters to encounter a series of electrical contacts 119. In this particular example, the header 120 includes a set screw block 124 at the distal side of the header 120 that may be tightened to fix the lead 106 in place once properly inserted but is otherwise uninvolved in the lead insertion detection.

The most proximal end connector 118 of the lead 106 is intended to ultimately connect to a proximal contact 122 of the header 120. A connection between the connector 118 and the contact 122 is an indicator that the lead 106 may be fully inserted on a gross scale. However, to more precisely determine proper lead insertion, another proximal contact 123 is adjacent to the proximal contact 122. In this particular example, the proximal contact 123 is proximal to the proximal contact 122. The contact 123 is spaced from the proximal contact 122 so that a voltage potential may be applied between the two. The spacing of a gap 121 is chosen so that the longitudinal dimension of the connector 118 is large enough to span the gap 121 between the contact 122 and the contact 123 and maintain a connection with both contacts 122, 123 at one time as shown in FIG. 2B.

The medical device 104 detects that continuity is established between the contacts 122, 123 when the connector 118 bridges the gap 121 between them to allow current to flow between the contacts 122, 123 during the monitoring due to the presence of the voltage potential. The connector 118 completes the circuit between the contacts 122, 123 without the need for current to pass through a conductor 109 of the lead 106 to a corresponding electrode 107. Therefore, the lead insertion detection proceeds regardless of the conditions where the distal end of the lead 106 is located.

The medical device 104 recognizes the flow of current between the contacts 122, 123 as an indication that the lead is fully inserted. In embodiments where the proximal contact 123 is proximal to the proximal contact 122, the presence of continuity between the contacts 122, 123 provides assurance that the connector 118 has a very robust connection to the proximal contact 122 considering the connector 118 has not merely made initial contact with the proximal contact 122 but has passed completely through the proximal contact 122 in order to reach the proximal contact 123. Thus, slight movements of the lead 106 within the header 120 in the future are unlikely to disrupt the connectivity of the connector 118 to the proximal contact 122. However, it will be appreciated that in other embodiments, proximal contact 123 can be distal of proximal contact 122 in order to detect continuity that is representative of full lead insertion.

According to some embodiments, the proximal contact 123 may be constructed with a longitudinal dimension, which is the dimension along the length of the lead 106, that is significantly less than that of the proximal contact 122. The proximal contact 122 may be constructed with a longitudinal dimension that is smaller than other proximal contacts so that the sum of the longitudinal dimensions of the contacts 122, 123 plus the length of the gap 121 between them is about the same as the longitudinal dimension of other contacts of the header 120. In this manner, the proximal connector 118 need not have a greater longitudinal dimension than any other connector of the lead 106. However, according to some embodiments, the connector 118 intended to bridge the gap 121 between adjacent contacts being used to detect continuity representative of proper lead insertion may have a greater longitudinal dimension than other connectors to account for any increase in the longitudinal dimension for the adjacent contacts and the gap 121 between them relative to that of a conventional proximal contact.

While this example has been described in the context of placing the adjacent contacts being monitored for continuity at the proximal end of the header 120, the adjacent contacts may additionally or alternatively be positioned at other locations within the header 120. For instance, the adjacent contacts may be positioned at a mid-point of the header 120 or may be positioned at the distal end of the header 120. However, placing the adjacent contacts at the proximal end of the header 120 ensures that there will not be any instances of continuity during lead insertion until the proximal end of the lead 106 has become fully inserted by reaching the proximal end of the header 120. For placement of the adjacent contacts in areas other than the proximal end of the header 120, it may be desirable to create a gap between the contacts that is too large for other connectors to span and include a connector with a larger longitudinal dimension than other connectors so that only the larger longitudinal connector may span the gap between the adjacent contacts. This configuration prevents smaller connectors from triggering false positives during the insertion as they pass by the adjacent contacts.

Furthermore, in this example, the proximal contact 122 is a contact that is also used for the stimulation and/or sensing being done by the medical device 104 to provide medical therapy where the connector 118 has the corresponding electrode 107 on the distal end with the electrical conductor 109 interconnecting the connector 118 and the electrode 107. The proximal contact 123 is dedicated to the lead insertion detection and is either not active for sensing/stimulation or is a duplicate signal of that being applied at the proximal contact 122. However, it will be appreciated that for some embodiments, the proximal contact 122 may also be a dedicated contact for the lead insertion procedure and that the connector 118 is dedicated to the lead insertion procedure as well such that there is no corresponding electrode on the distal end.

Figure 3A:
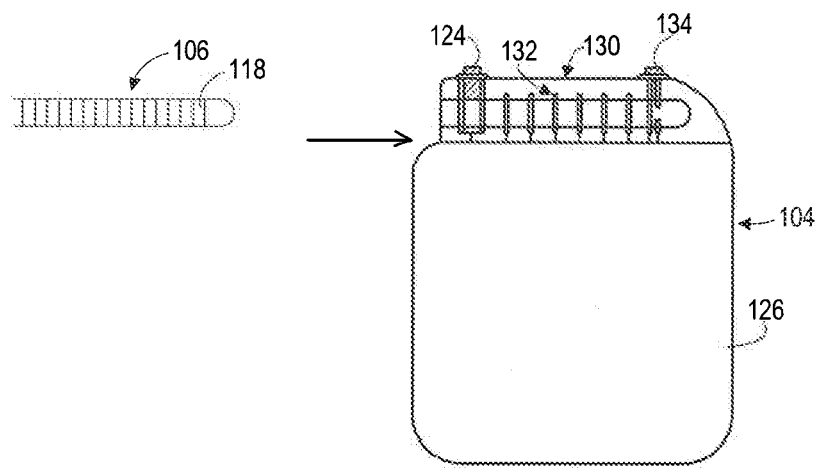
FIG. 3A shows a proximal end of an implantable lead and another example of a header of a medical device that receives the proximal end to complete electrical connections to a set screw connector block contact.
Figure 3B:
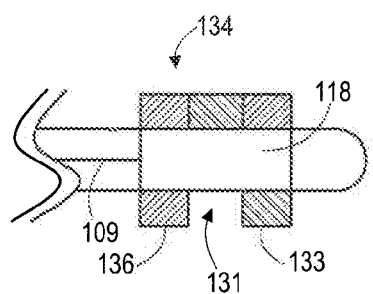
FIG. 3B shows an enlarged view of the proximal end contact portions of a set screw block contact and an electrical connector from the example of FIG. 3A.

FIGS. 3A and 3B show a proximal end of the lead 106 as the lead 106 is being inserted into a header 130 of the medical device 104 that utilizes a set screw block contact for detecting proper lead insertion. As in the example of FIG. 2A, the header 130 is mounted to the can 126 which encloses the electrical circuitry of the medical device 104. The header 130 includes a passageway that the lead 106 enters to encounter a series of electrical contacts 132. In this particular example, the header 130 includes a set screw block 134 at the proximal side of the header 130 that may be tightened to fix the lead 106 in place once properly inserted but is also involved in the lead insertion detection.

The most proximal end connector 118 of the lead 106 is intended to ultimately connect to the set screw block contact 134 of the header 130. A connection between the connector 118 and the contact 134 is an indicator that the lead 106 may be fully inserted on a gross scale. However, to more precisely determine proper lead insertion, another proximal contact 133 is integrated with the set screw block contact 134. In this particular example, the set screw block contact 134 has a first portion 136 while the proximal contact 133 forms a second portion that is electrically isolated from the first portion 136. In this example, the proximal contact 133 is proximal to the first portion 136 but it will be appreciated that the proximal contact 133 may be distal relative to the first portion 136 and still allow for detection of continuity between the proximal contact 133 and the first portion 136. The contact 133 is isolated from the first portion 136 so that a voltage potential may be applied between the two. The spacing of a gap 131 is chosen so that the longitudinal dimension of the connector 118 is large enough to span the 131 gap between the contact 136 and the contact 133 and maintain a connection with both contact portions 136, 133 at one time.

The medical device 104 detects that continuity is established between the contacts 136, 133 when the connector 118 bridges the gap 131 between them to allow current to flow between the contacts 136, 133 during the monitoring due to the presence of the voltage potential. The connector 118 completes the circuit between the contacts 136, 133 without the need for current to pass through the electrical conductor 109 of the lead 106 to the corresponding electrode 107. Therefore, the lead insertion detection proceeds regardless of the conditions where the distal end of the lead 106 is located.

The medical device 104 recognizes the flow of current between the contacts 136, 133 as an indication that the lead is fully inserted. In embodiments where the proximal contact 133 is proximal to the proximal contact 136, the presence of continuity between the contacts 136, 133 provides assurance that the connector 118 has a very robust connection to the proximal contact 136 considering the connector 118 has not merely made initial contact with the proximal contact 136 but has passed completely through the proximal contact 136 in order to reach the proximal contact 133. Thus, slight movements of the lead 106 within the header 130 in the future are unlikely to disrupt the connectivity of the connector 118 to the proximal contact 136.

As the proximal contact 133 may be constructed as a portion of the set screw block contact 134, the size of the set screw block contact 134 including both the proximal contact portions 136, 133 may have about the same longitudinal dimension as that of other contacts of the header 130. In this manner, the proximal connector 118 need not have a greater longitudinal dimension than any other connector of the lead 106.

While this example has been described in the context of placing the set screw block contact 134 being monitored for continuity at the proximal end of the header 130, the set screw connector block contact 134 may additionally or alternatively be positioned at other locations within the header 130. For instance, the set screw connector block contact 134 may be positioned at a mid-point of the header 130 or may be positioned at the distal end of the header 130 such as in place of the set screw block 124 or in addition to the set screw block 124. However, placing the set screw block contact 134 that is being monitored for continuity at the proximal end of the header 130 ensures that there will not be any instances of continuity during lead insertion until the proximal end of the lead 106 has become fully inserted by reaching the proximal end of the header 130.

Furthermore, in this example, the proximal contact portion 136 of the set screw block contact 134 is a contact that is also used for the stimulation and/or sensing being done by the medical device 104 to provide medical therapy where the connector 118 has the corresponding electrode 107 on the distal end with the electrical conductor 109 interconnecting the connector 118 to the electrode 107. The proximal contact portion 133 of the set screw block contact 134 is dedicated to the lead insertion detection and is either not active for sensing/stimulation or is a duplicate signal of that being applied at the proximal contact portion 136. However, it will be appreciated that for some embodiments, the proximal contact portion 136 may also be a dedicated contact for the lead insertion procedure and that the connector 118 is dedicated to the lead insertion procedure as well such that there is no corresponding electrode on the distal end.

Figure 4:
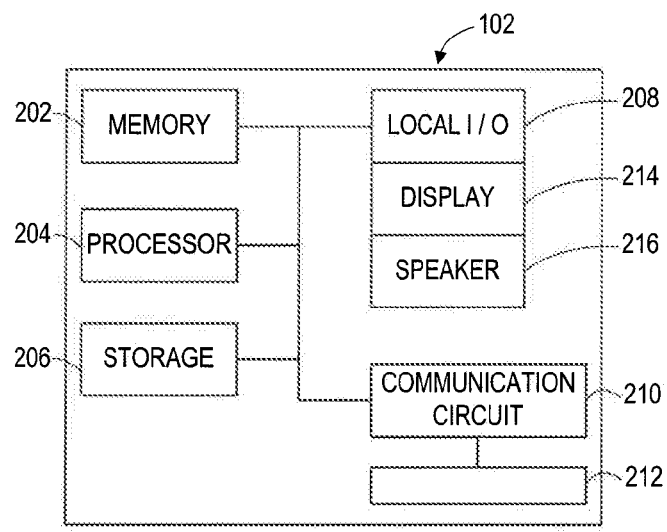
FIG. 4 shows an illustrative external device embodiment that communicates with a medical device to initiate the detection of proper lead insertion according to various embodiments.

FIG. 4 shows components of one example of the external device 102. The external device 102 includes a memory 202, a processor 204, and may also include a storage device 206. The external device 102 may also include local input/output (I/O) ports 208 such as to provide local screen displays on a display device 214, to provide sound via a speaker 216, and to receive user input via a keypad, touchscreen, and so forth. The external device 102 also includes communication circuitry 210 used to establish the telemetry to the medical device 104. For instance, the communication circuitry 210 may drive a signal propagation tool 212, such as an RF antenna or an arm's length inductive coupling head.

The memory 202 may be used to store information in use by the processor 204. For instance, the memory 202 may also store programming that is used by the processor 204 to control the actions of the external device 102 that take place to detect proper lead 106 insertion. The memory 202 may be of various types, such as volatile, non-volatile, or a combination of the two.

The storage device 206 may be used to store information for a long term and may be of various types such as non-volatile so that the information is retained when the external device 102 is powered off. The storage device 206 may also store programming for the processor 204 that is implemented to control the verification actions. Examples of the storage device 206 include electronic, magnetic, and optical drives. The storage device 206 and the memory 202 are both examples of computer readable media that may store information in the form of computer programming, data structures, and the like.

Figure 6:
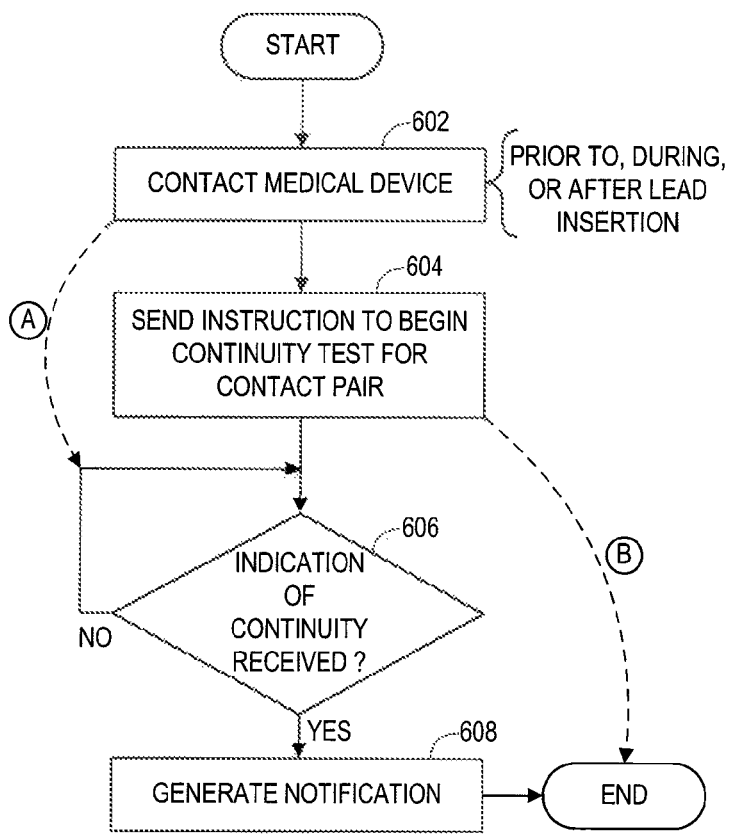
FIG. 6 shows an example of operational flow of external device embodiments that communicate with a medical device to detect proper lead insertion.

The processor 204 performs logical operations such as those of FIG. 6 to allow the external device 102 to communicate with the medical device 104 to initiate the detection of proper lead insertion and/or to receive notification of continuity of the adjacent contacts from the medical device 104. The processor 204 may perform additional logical operations to provide an output of information such as a visual display or audible signal indicating that the lead 106 is properly inserted. The processor 204 may be of various forms. For instance, the processor 204 may be a general-purpose programmable processor that executes software that is stored on the storage device 206 or elsewhere. Other examples include a dedicated purpose hardware circuit or hard-wired digital logic. The processor 204 may communicate with the various other components through one or more data buses.

Figure 5A:
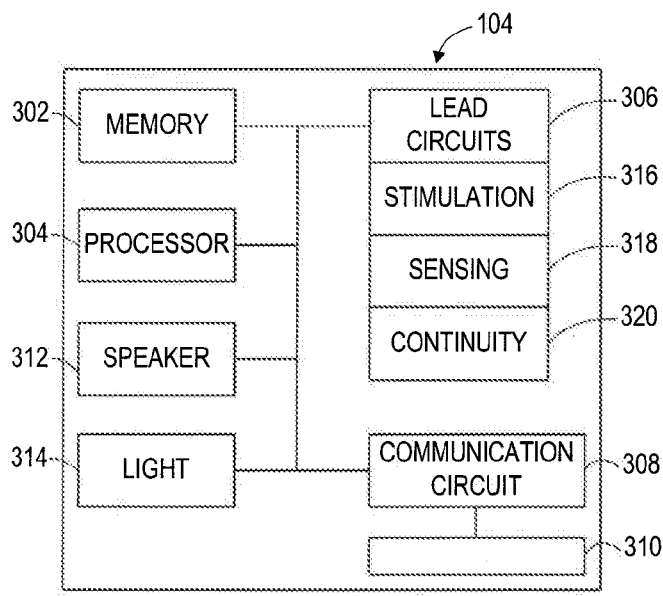
FIG. 5A shows an illustrative medical device embodiment that detects proper lead insertion and provides a related notification.

FIG. 5A shows components of one example of the medical device 104. The medical device 104 includes a memory 302 and a processor 304. The medical device 104 also includes lead circuitry 306 and the related conductors in the header. The lead circuitry performs medical tasks such as stimulation via stimulation circuitry 316 and/or monitoring via monitoring circuitry 318 but also performs the continuity monitoring for the various combinations of lead connectors during the detection of proper lead insertion via lead detection circuitry 320. The medical device 104 also includes communication circuitry 308 used to establish the telemetry to the external device 102. The communication circuitry 308 may drive a signal propagation tool 310, such as an integral RF antenna or an integrated arm's length inductive coupling head.

The lead may also include notification elements. One such element may be a transducer 312 such as a piezoelectric speaker that makes a tone to provide a notification that continuity of the adjacent contacts has occurred. Another element may be a light 314 that may illuminate and/or flash to provide a notification that continuity of the adjacent contacts has occurred.

The memory 302 may be used to store information in use by the processor 304 such as programming and data values including the continuity monitoring and notification information. The memory 302 may store additional information including therapy parameters that are used to control the lead circuitry 306. The memory 302 may be of various types such as volatile, non-volatile, or a combination of the two. The memory 302 is also an example of computer readable media that may store information in the form of computer programming, data structures, and the like.

The processor 304 performs logical operations to allow communication sessions with the external device 102. In some embodiments, the communication session may be used in order to initiate the continuity monitoring procedure for detecting proper lead insertion and/or to send a notification that continuity has occurred back to the external device 102. The processor 304 may be of various forms like those discussed above for the processor 204 of the external device 102. The processor 304 may communicate with the various other components through one or more data buses.

Figure 5B:
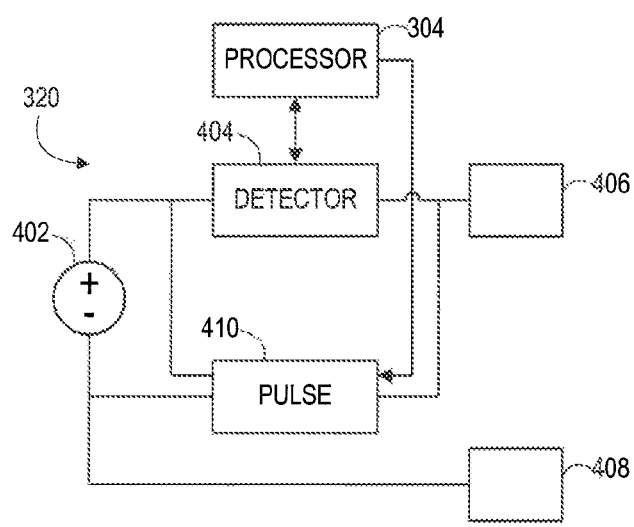
FIG. 5B shows an example of lead monitoring circuitry of the medical device embodiment of FIG. 5A.

FIG. 5B shows an example of lead monitoring circuitry 320 of embodiments of the medical device 104. The lead monitoring circuitry 320 includes a continuity detector 404 that receives a voltage from a power source 402 and provides a voltage to a terminal 406. The terminal 406 represents a contact within the header that is being used to test for continuity. As shown, the power source 402 is a battery. This battery may be the primary battery of the medical device 104 that is used to power the electrical components as well as provide power for generation of the stimulation signals. Rather than a voltage source, the power source 402 may be a current source. There may also be intervening circuitry such as voltage or current regulators. The power source 402 is also electrically connected to another terminal 408 that represents the other contact within the header that is being used to test for continuity.

The detector 404 may be in communication with the processor 304 in order to begin continuity testing. The detector 404 may control application of voltage to the terminal 406 accordingly. When no power is necessary, such as during normal implanted operation of the medical device 104, the detector 404 may block the voltage to the terminal 406 so that the terminal 406 may be used for stimulation without interference from power being applied for continuity detection. The detector 404 may otherwise apply the power for continuity testing to the terminal 406.

The processor 304 and detector 404 may be configured so that during shelf mode, the detector applies voltage to the terminal 406. As no conductor is present between the terminals 406 and 408, little to no current draw will occur so that the battery 402 is not depleted. In this manner, the medical device 104 is already performing continuity testing without regard to contact from an external device 102 during lead insertion. However, the processor 304 and detector 404 may be configured so that the detector 404 does not apply power until the processor 304 receives an instruction to begin continuity testing from an external device 102.

During continuity testing, the detector 404 monitors for the flow of current to terminal 406. When the lead 106 is not fully inserted, an open circuit remains between terminals 406 and 408 and no current flows. The processor 304 continues to await a signal from the detector 404 indicating continuity and thus no notification is provided. Once the detector 404 detects current flow, which results from the presence of a lead connector 118 being present to interconnect terminals 406 and 408, a signal is sent to the processor 304 which may then generate a notification of continuity. At that point, the processor 304 may also signal the detector 404 to stop providing voltage to the terminal 406.

Also shown in FIG. 5B, a pulse generator 410 may be present as part of the stimulation circuit 316 to provide stimulation pulses to the terminal 406 if instructed to do so by the processor 304. The pulse generator 410 may be inactive during continuity testing and then may become active once the detector 404 no longer provides power to the terminal 406. For embodiments where both adjacent contacts used for continuity testing are dedicated to continuity testing, then a connection from the pulse generator 410 to the terminal 406 may be omitted.

FIG. 6 shows an example of logical operations that may be performed by embodiments of an external device 102. The external device 102 may be involved in the continuity testing to detect full lead insertion for various reasons. For example, the external device 102 may be involved only to initiate testing where the medical device 104 does not automatically perform the continuity testing but where the medical device 104 provides a visual and/or audible notification such that a notification from the external device 102 is not needed. As another example, the external device 102 may be involved only to provide a notification of full lead insertion once being informed of such by the medical device 104, where the medical device 104 may or may not have provided an audible or visual notification and where the medical device 104 initiated the continuity test without being instructed. As yet another example, the external device 102 may be involved where the external device 102 instructs the medical device 104 to begin continuity testing and where the external device 102 provides a notification upon being informed that continuity, and hence full lead insertion, has been achieved. These variations are illustrated as alternate operational flows within FIG. 6.

Initially, the external device 102 may contact the medical device 104 via telemetry at a communication operation 602. For external devices 102 that utilize RF or arm's length near field communications, this communication may occur before lead insertion begins, during lead insertion, or upon completion of lead insertion by the clinician. For external devices 102 that utilize near field communication, the communication may be done before insertion begins or after insertion is completed to avoid the telemetry head being in the physical space where the clinician is working with the medical device 104. For purposes of discussing communication between the external device 102 and the medical device 104, the completion of lead insertion is that point in time once the clinician believes the lead is fully inserted and is ready for a telemetry head, if necessary, to be positioned over the medical device 104.

After the external device 102 has had initial contact with the medical device 104 at the communication operation 602, for embodiments where the medical device 104 waits for an instruction for continuity testing, then the external device 102 sends an instruction to begin the continuity test for the contact pair at an instruction operation 604. The instruction may specify details of the notification such as whether to provide a notification via an audible or visual manner and/or whether to provide a telemetry signal as a notification.

For embodiments where the medical device 104 performs continuity testing without receiving an instruction, such as an automatic function when in shelf mode, but the external device 102 is involved in the notification process, then operational flow may proceed from the communication operation 602 directly to a query operation 606, discussed below, as shown for the alternate path A. If the external device 102 is not involved in initiating the continuity test or providing the notification of continuity, then the external device 102 may perform none of the operations of FIG. 6 as the medical device 104 may handle all aspects of detecting full lead insertion and providing a corresponding notification.

Returning to the example where the external device sends the instruction at the instruction operation 604, if the external device 102 will not receive a notification of continuity via telemetry, such as because the clinician will rely on an audible or visual notification at the medical device 104, then the operational flow of the external device 102 related to the continuity testing may end as shown for the alternate path B. Where the external device 102 will be involved in the notification aspect, then operational flow may then proceed to a query operation 606.

Regardless of the path to query operation 606, once here the external device 102 detects whether a notification of continuity has been received via telemetry from the medical device 104. The external device 102 may continue to wait until a notification is received, until a timeout has expired, or until a user manually ends the communication process with the medical device 104.

Upon detecting that a notification of continuity has been received via telemetry from the medical device 104, the external device 102 may then generate a notification to the local user at a notification operation 608. This notification may be of various forms such as audible and/or visual to alert the local user of the external device 102 that continuity has been achieved. This notification by the external device 102 may be noticeable by the clinician, or the local user of the external device 102 may inform the clinician of the notification such as where the medical device 104 does not generate an audible or visual notification or where the clinician has not noticed the notification.

For embodiments where the external device 102 instructs the medical device 104 to begin continuity detection at the instruction operation 604 after lead insertion has completed, the feedback as to whether the lead is inserted fully or not occurs after the clinician believes the lead insertion has completed. If a notification of full lead insertion is not being provided either by the medical device 104 or the external device 102 because continuity has not been detected, then the clinician will return to the medical device 104 and re-attempt to fully insert the lead 106.

For embodiments where the notification is via near field telemetry, regardless of whether an instruction is required to start the detection of continuity, then once the clinician believes lead insertion is complete and allows the telemetry head to be returned to the medical device 104 a determination can be made as to whether a notification of full lead insertion has occurred. The telemetry head is moved into position, and the local user monitors the external device 102 for a notification. If the notification is not being provided because continuity has not been detected, then the clinician 104 will again have to re-attempt lead insertion and subsequently allow the telemetry head to be positioned near the medical device 104 to determine if a notification of continuity is being generated. If no notification occurs during this re-attempt, then the clinician may again approach the medical device 104 and perform another re-attempt. This process may repeat until a notification of continuity is provided.

For embodiments where the medical device 104 performs continuity testing in response to an instruction received after completion of lead insertion and where notifications are provided other than by near field telemetry, the clinician may receive real time feedback during the insertion re-attempt. This real time feedback on the re-attempt may be possible because the medical device 104 has already been instructed to perform the continuity testing and provide a notification of continuity. As the clinician may continue with the lead insertion re-attempt until the notification of full lead insertion is generated, a second re-attempt is unnecessary.

For embodiments where the medical device 104 performs continuity testing without an instruction or in response to an instruction received before completion of lead insertion and where the medical device 104 provides a notification other than by using near field telemetry, then real time feedback may be provided during the initial insertion attempt. As the clinician may continue with the lead insertion process until the notification of full lead insertion is generated, a re-attempt is unnecessary.

Upon the notification of full lead insertion being provided, the clinician may proceed with subsequent implantation steps. These may include locking the lead 106 in place within the header 120, 130 via a set screw or other mechanism. Other steps may include handling any slack in the lead 106 such as by wrapping the excess amount around the medical device 104, and ultimately implanting the medical device 104 into a pocket formed within the tissue of the patient.

Figure 7:
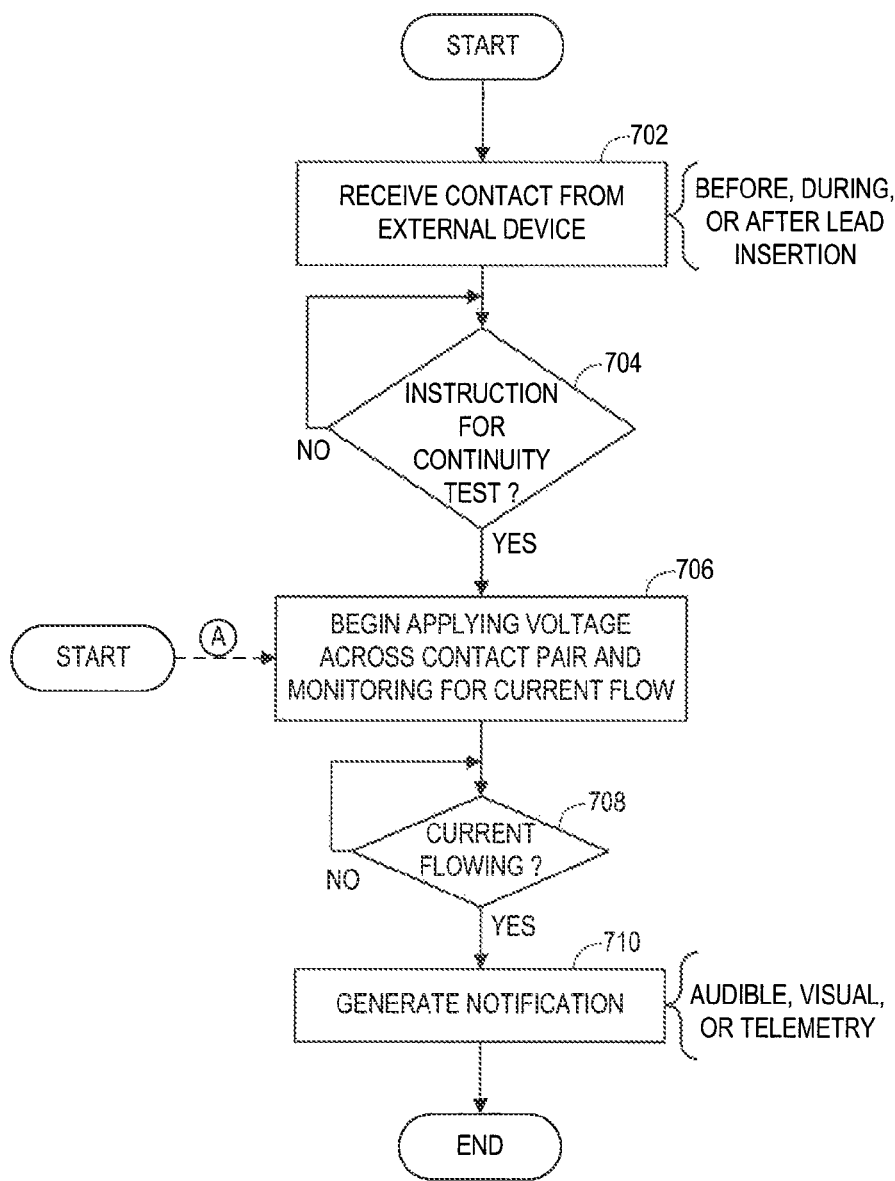
FIG. 7 shows an example of operational flow of medical device embodiments that detect proper lead insertion and provide a related notification.

FIG. 7 shows an example of logical operations that may be performed by embodiments of the medical device 104 to test for continuity of the adjacent contacts and provide a related notification when continuity is achieved. As discussed above in relation to FIG. 6, the external device 102 may be involved in the continuity testing to detect full lead insertion for various reasons and the operations of the medical device 104 may vary depending upon the involvement of the external device 102. The medical device 104 may require that an instruction be received from the external device 102 prior to beginning continuity testing but may provide a visual and/or audible notification such that a notification to the external device 102 is not needed. As another example, the medical device 104 may provide a telemetry notification to the external device 102, where the medical device 104 may or may not have provided an audible or visual notification and where the medical device 104 initiated the continuity test without being instructed. As yet another example, medical device 104 may require an instruction be received before beginning continuity testing and may also provide a telemetry notification where the medical device 104 may or may not have provided an audible or visual notification. As another example, the medical device 104 may have no interaction with the external device 102 regarding the continuity testing as the medical device initiates the continuity testing without instruction and provides a local notification without sending a telemetry notification. These variations are illustrated as alternate operational flows within FIG. 7.

According to embodiments where the medical device 104 requires an instruction to begin testing for continuity, the medical device 104 receives contact from an external device 102 either before, during, or after lead insertion at a communication operation 702. The medical device 104 then detects whether an instruction to begin the continuity testing has been received during the communication from the external device 102 at a query operation 704. If not, then the medical device 104 awaits the instruction.

The medical device 104 begins the continuity test by applying voltage across the adjacent contacts and monitoring for current flow indicative of continuity at a test operation 706. For embodiments where the medical device 104 requires the instruction from the external device 102 to begin continuity testing, then the test operation 706 may begin once the medical device 104 has detected the instruction at the query operation 704. For embodiments where the medical device 104 does not require the instruction, such as where the medical device 104 automatically performs the continuity testing while in shelf mode, then the medical device 104 performs the test operation 706 from the start as shown in alternate path A.

At a query operation 708, the medical device 104 detects from the monitoring whether current is flowing between the adjacent contacts. If no current is flowing, then the medical device continues the test operation 708 until current flow is detected. Once current flow is detected, the medical device 104 then generates a notification of full lead insertion at a notification operation 710. The notification may be a local audible or visual notification. Additionally or alternatively, the notification may be a telemetry notification signal to the external device 102. In the case of a telemetry notification signal, this notification may be sent immediately where a communication session exists or may be queued until a communication session is established with the external device 102. The telemetry notification being queued until a communication session is later established may be particularly applicable for embodiments where near field telemetry is being used or where alternate path A has been followed and a communication session has not been established prior to the lead insertion process completing.

While embodiments have been particularly shown and described, it will be understood by those skilled in the art that various other changes in the form and details may be made therein without departing from the spirit and scope of the invention.

What is claimed is:

1. A method of detecting that a medical lead has been fully inserted into a medical device, comprising:
   providing a set screw block with first and second portions that are electrically isolated from one another, the first portion forming a first electrical contact and the second portion forming a second electrical contact, the first and the second electrical contacts being adjacent and electrically isolated from each other where a spacing between the first and second electrical contacts allows for an electrical connector of the medical lead to maintain physical contact with both the first and second electrical contacts at one time;
   during lead insertion, monitoring for electrical continuity between the first and second electrical contacts; and
   providing a notification upon detecting electrical continuity between the first and second electrical contacts.

2. The method of claim 1, further comprises providing the first electrical contact with a connection to medical circuitry of the medical device.

3. The method of claim 1, wherein the medical device comprises stimulation circuitry.

4. The method of claim 1, wherein the second electrical contact is proximal to the first electrical contact.

5. The method of claim 1, further comprising providing the first electrical contact with a connection to lead insertion monitoring circuitry.

6. The method of claim 1, wherein monitoring for electrical continuity comprises applying a voltage potential from the lead insertion monitoring circuitry between the first and second electrical contacts and monitoring for electrical current flow between the first and second electrical contacts at the lead insertion monitoring circuitry.

7. The method of claim 1, wherein the notification is visual.

8. The method of claim 1, wherein the notification is audible.

9. The method of claim 1, wherein the notification is a telemetry message.

10. The method of claim 1, where the medical device includes a header that contains the first and second electrical contacts and a plurality of additional electrical contacts and wherein the first and second electrical contacts are proximal to the plurality of electrical contacts.

11. An implantable medical device, comprising:
    a header;
    a plurality of electrical contacts within the header, wherein the plurality of electrical contacts comprises a set screw block with first and second portions that are electrically isolated from one another, the first portion forming a first electrical contact and the second portion forming a second electrical contact, the first electrical contact and the second electrical contact being adjacent and electrically isolated from each other where a spacing between the first and second electrical contacts allows for an electrical connector of a medical lead to maintain physical contact with both the first and the second electrical contacts at one time;
    medical circuitry electrically connected to at least one of the electrical contacts of the plurality; and
    lead insertion monitoring circuitry electrically connected to the first and second electrical contacts, wherein during lead insertion, the lead insertion monitoring circuitry monitors for electrical continuity between the first and second electrical contacts and provides a notification upon detecting electrical continuity between the first and second electrical contacts.

12. The implantable medical device of claim 11, wherein the first electrical contact has a connection to the medical circuitry.

13. The implantable medical device of claim 11, wherein the medical circuitry comprises stimulation circuitry.

14. The implantable medical device of claim 11, wherein the second electrical contact is proximal to the first electrical contact.

15. The implantable medical device of claim 11, wherein the lead insertion monitoring circuit applies a voltage potential between the first and second electrical contacts and monitors for electrical current flow between the first and second electrical contacts.

16. The implantable medical device of claim 11, further comprising a light and wherein the lead monitoring circuit utilizes the light to provide a notification that is visual.

17. The implantable medical device of claim 11, further comprising a speaker and wherein the lead monitoring circuit utilizes the speaker to provide a notification that is audible.

18. The implantable medical device of claim 11, further comprising a telemetry circuit and wherein the lead monitoring circuit utilizes the telemetry circuit to provide a notification that is a telemetry message.

19. The implantable medical device of claim 11, wherein the first and second electrical contacts are proximal to other electrical contacts of the plurality of electrical contacts.

20. A medical system comprising:
    an implantable medical device that comprises:
    a header;
    a plurality of electrical contacts within the header, wherein the plurality of electrical contacts comprises a set screw block with first and second portions that are electrically isolated from one another, the first portion forming a first electrical contact and the second portion forming a second electrical contact, the first electrical contact and the second electrical contact being adjacent and electrically isolated from each other,
    wherein the implantable medical device, during lead insertion, monitors for electrical continuity between the first and second electrical contacts and provides a notification upon detecting electrical continuity between the first and second electrical contacts; and
    an implantable medical lead that has a proximal end positioned within the header and comprises:
    a lead body;
    a plurality of connectors on the proximal end, wherein one connector of the plurality maintains physical contact with both the first and the second electrical contacts at one time;
    a plurality of electrodes on a distal end; and
    electrical conductors within the lead body providing an electrical pathway between the connectors and the electrodes.

21. The medical system of claim 20, wherein the implantable medical device further comprises medical circuitry and wherein the first electrical contact has a connection to the medical circuitry.

22. The medical system of claim 21, wherein the medical circuitry comprises stimulation circuitry.

23. The medical system of claim 20, wherein the second electrical contact is proximal to the first electrical contact.

24. The medical system of claim 20, wherein the implantable medical device further comprises lead insertion monitoring circuit that applies a voltage potential between the first and second electrical contacts and monitors for electrical current flow between the first and second electrical contacts.

25. The medical system of claim 20, wherein the implantable medical device further comprises a light and wherein the lead monitoring circuit utilizes the light to provide a notification that is visual.

26. The medical system of claim 20, wherein the implantable medical device further comprises a speaker and wherein the lead monitoring circuit utilizes the speaker to provide a notification that is audible.

27. The medical system of claim 20, wherein the notification is a telemetry message.

28. The medical system of claim 20, wherein the first and second electrical contacts are proximal to other electrical contacts of the plurality of electrical contacts.

29. The medical system of claim 20, further comprising an external device that includes telemetry circuitry and that instructs the implantable medical device via telemetry signals to begin monitoring for lead insertion, wherein the implantable medical device further comprises a telemetry circuit and wherein the implantable medical device utilizes the telemetry circuit to receive the telemetry signals from the external device.

30. The medical system of claim 29, wherein the implantable medical device utilizes the telemetry circuitry to provide a notification that is a telemetry message that is received by the external device, and wherein the external device provides a notification upon receiving the telemetry message.

31. The medical system of claim 30, wherein the external device further comprises a visual indicator and wherein the notification provided by the external device is visual.

32. The medical system of claim 30, wherein the external device further comprises a speaker and wherein the notification provided by the external device is audible.

33. A medical system comprising:
an implantable medical device that comprises:
a header;
a plurality of electrical contacts within the header, wherein the plurality of electrical contacts comprises a first electrical contact and a second electrical contact being adjacent and electrically isolated from each other,
wherein the implantable medical device, during lead insertion, monitors for electrical continuity between the first and second electrical contacts and provides a notification upon detecting electrical continuity between the first and second electrical contacts; and
an implantable medical lead that has a proximal end positioned within the header and comprises:
a lead body;
a plurality of connectors on the proximal end, wherein one connector of the plurality maintains physical contact with both the first and the second electrical contacts at one time;
a plurality of electrodes on a distal end; and
electrical conductors within the lead body providing an electrical pathway between the connectors and the electrodes;
an external device that includes telemetry circuitry and that instructs the implantable medical device via telemetry signals to begin monitoring for lead insertion, wherein the implantable medical device further comprises a telemetry circuit and wherein the implantable medical device utilizes the telemetry circuit to receive the telemetry signals from the external device.

34. An implantable medical device, comprising:
a header;
a plurality of electrical contacts within the header, wherein the plurality of electrical contacts comprises a first electrical contact and a second electrical contact being adjacent and electrically isolated from each other where a spacing between the first and second electrical contacts allows for an electrical connector of a medical lead to maintain physical contact with both the first and the second electrical contacts at one time;
medical circuitry electrically connected to at least one of the electrical contacts of the plurality;
telemetry circuitry;
lead insertion monitoring circuitry electrically connected to the first and second electrical contacts and to the telemetry circuitry, wherein the telemetry circuitry receives an instruction to being monitoring for lead insertion, and wherein in response to receiving the instruction the lead monitoring circuitry begins to monitor for electrical continuity between the first and second electrical contacts and provides a notification upon detecting electrical continuity between the first and second electrical contacts.

35. A method of detecting that a medical lead has been fully inserted into a medical device, comprising:
providing a first and a second electrical contact within the medical device, the first and the second electrical contacts being adjacent and electrically isolated from each other where a spacing between the first and second electrical contacts allows for an electrical connector of the medical lead to maintain physical contact with both the first and second electrical contacts at one time;
receiving telemetry signals at the medical device, the telemetry signals including an instruction to begin monitoring for lead insertion;
in response to receiving the instruction, monitoring by the medical device for electrical continuity between the first and second electrical contacts; and
providing a notification upon detecting electrical continuity between the first and second electrical contacts.

* * * * *